United States Patent [19]

Watanabe et al.

[11] Patent Number: 5,698,575

[45] Date of Patent: Dec. 16, 1997

[54] CHROMONE COMPOUNDS, PHARMACEUTICAL COMPOSITIONS CONTAINING THE SAME, AND USE OF THE SAME

[75] Inventors: Koju Watanabe, Saitama; Tsuyoshi Saito, Ibaraki; Koichi Niimura, Saitama, all of Japan

[73] Assignee: Kureha Chemical Industry Co., Ltd., Tokyo, Japan

[21] Appl. No.: 694,934

[22] Filed: Aug. 9, 1996

[30] Foreign Application Priority Data

Aug. 10, 1995 [JP] Japan ................................ 7-225875

[51] Int. Cl.⁶ ........................................... C07D 407/04
[52] U.S. Cl. ..................... 514/383; 514/394; 514/406; 514/414; 514/422; 548/256; 548/266.4; 548/305.1; 548/361.1; 548/364.4; 548/464; 548/525
[58] Field of Search ........................ 514/383, 394, 514/406, 422, 414; 548/256, 305.1, 364.4, 361.1, 464, 525, 266.4

[56] References Cited

FOREIGN PATENT DOCUMENTS

| 0247760 | 12/1987 | European Pat. Off. . |
|---|---|---|
| 90/06921 | 6/1990 | WIPO . |

OTHER PUBLICATIONS

Bantick et al, *Journal of Heterocyclic Chemistry*, 18(4):679–683 (1981).

Mazzei et al, *Chemical Abstracts*, 106(3):582, Abstract No. 18313w (1987).

Mazzei et al, *Chemical Abstracts*, 105(9):634, Abstract No. 78797w (1986).

Ellis et al., Benzopyrones, J.C.S. Perkin I, 2557–2560, 1981.

Reddy et al., Chemical Abstracts, vol. 83:114280k, 1975.

*Primary Examiner*—Joseph McKane
*Attorney, Agent, or Firm*—Sughrue, Mion, Zinn, Macpeak & Seas, PLLC

[57] ABSTRACT

A chromone derivative of the formula (I):

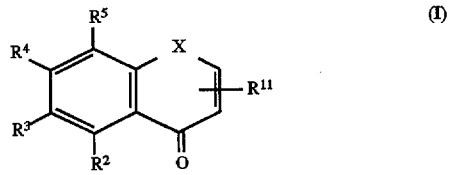

wherein $R^{11}$ is a pyrazolyl, pyrrolyl, triazolyl, benzotriazolyl, benzimidazolyl, indazolyl, or indolyl group, $R^2$, $R^3$, $R^4$, and $R^5$ is independently a hydrogen or halogen atom, or a hydroxy or alkoxy group, or an alkoxy group substituted with one or more alkoxy groups, and X is an oxygen or sulfur atom, or a salt thereof is disclosed. The chromone derivative inhibits the activity of matrix metalloproteinase.

6 Claims, 3 Drawing Sheets

CHROMONE COMPOUNDS, PHARMACEUTICAL COMPOSITIONS CONTAINING THE SAME, AND USE OF THE SAME

BACKGROUND OF THE INVENTION

1. Field of the Invention

The present invention relates to a chromone derivative, a process for preparing the same, a pharmaceutical composition, particularly an agent for inhibiting matrix metalloproteinase, containing the chromone derivative or a pharmaceutically acceptable salt thereof, and use of the chromone derivative.

2. Description of the Related Art

A matrix metalloproteinase (hereinafter sometimes referred to as MMPs) is a general name of a metallic enzyme to digest protein moieties of an extracellular matrix. The MMPs are generally classified into four groups: collagenases, such as interstitial collagenase (MMP-1) and leukocyto collagenase (MMP-8); gelatinases/type-IV collagenases, such as gelatinase A (MMP-2) and gelatinase B (MMP-9); stromelysins, such as stromelysin-1 (MMP-3), stromelysin-2 (MMP-10) and stromelysin-3 (MMP-11); and others, such as matrilysin (MMP-7).

Recently, the relationship between the MMPs and various diseases has been slowly resolved. For example, Okada reported in "Matrix metalloproteinases in inflammation", Soshiki-Baiyo (Tissue Culture), 19(11)386–390, 1993, the possibility that MMPs are deeply involved in a pathologic tissue, such as synovial membrane and articular cartilage tissue of rheumatoid arthritis or osteoarthritis, cornea ulcer, wound healing, granuloma, periodontitis, vesicular exanthem, glomerular nephritis, pulmonary emphysema, pathologic bone resorption, infiltration or metastasis of cancer tissue. For example, a rise of MMPs production in tumor tissues or inflamed lesions was proved in gene and protein levels. Therefore, substances capable of inhibiting the production or activity of MMPs are expected to exhibit functions effective to the various diseases.

Hitherto, as an inhibitor of the matrix metalloproteinase, peptides having the structure similar to that of the substrate for the matrix metalloproteinase (for example, Japanese Unexamined International Patent Publication no. 4-501423), or hydroxamic acid (for example, Japanese Unexamined Patent Publication No. 6-256293) were known. However, they were disadvantageously susceptible to hydrolysis, and thus hard to maintain their activities.

As a compound having a chromone skeleton, for example, Japanese Unexamined Patent Publication No. 4-502322 discloses compounds having a chromone skeleton which carries, at 2-position thereof, a residue of a nitrogen-containing compound, such as a morpholino or 4-methyl-1-piperazinyl group, and its functions of anti-atherosclerosis and anti-thrombus. Further, compounds having a chromone or thiochromone skeleton which carries an imidazolyl group [P. Cozzi et al., J. Heterocycl. Chem. (1985) Vol. 22, No. 2, pp. 441–443, and P. Cozzi et al., J. Heterocycl. Chem. (1988) Vol. 25, No. 6, pp. 1613–1616].

SUMMARY OF THE INVENTION

The inventors of the present invention engaged in intensive researches on the compounds which exhibit inhibitory activity to the matrix metalloproteinase, but have chemical structures different from those of the known peptide-compounds, and as a result, found that novel chromone compounds having a chemical structure different from those of the known chromone compounds exhibits inhibitory activity to the matrix metalloproteinase, and is stable in a living body after administration, and thus the inhibitory activity to the matrix metalloproteinase is maintained.

Therefore, the object of the present invention is to provide the novel chromone compounds which exhibit inhibitory activity to the matrix metalloproteinase.

Other objects and advantages will be apparent from the following description.

In accordance with the present invention, there is provided a chromone derivative of the formula (I):

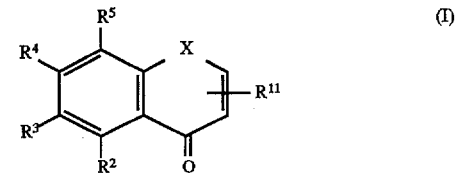

wherein $R^{11}$ is a pyrazolyl, pyrrolyl, triazolyl, benzotriazolyl, benzimidazolyl, indazolyl, or indolyl group, $R^2$, $R^3$, $R^4$, and $R^5$ is independently a hydrogen or halogen atom, or a hydroxy or alkoxy group, or an alkoxy group substituted with one or more alkoxy groups, and X is an oxygen or sulfur atom, or a salt thereof.

The present invention also relates to a process for preparing a compound of the formula (IA):

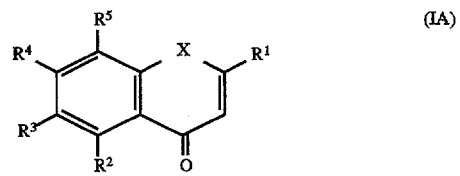

wherein $R^1$ is a residue of a nitrogen-containing heterocyclic compound, and $R^2$, $R^3$, $R^4$, $R^5$ and X have the meanings as above, comprising reacting a compound of the formula (II):

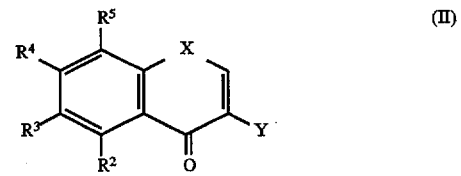

wherein $R^2$, $R^3$, $R^4$, $R^5$ and X have the meanings as above, and Y is a halogen atom, and a compound of the formula (III):

$$R^1H \qquad (III)$$

wherein $R^1$ has the meanings as above, in the presence of a base.

Further, the present invention relates to a process for preparing a compound of the formula (IB):

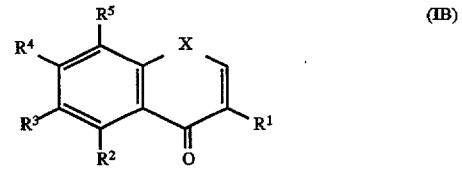

wherein $R^1$, $R^2$, $R^3$, $R^4$, $R^5$ and X have the meanings as above, comprising reacting a compound of the formula (IV):

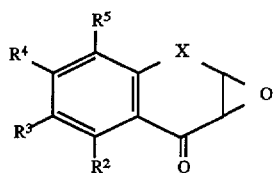

(IV)

wherein $R^2$, $R^3$, $R^4$, $R^5$ and X have the same meanings as above, and the compound of the formula (III), in the presence of a base.

Still further, the present invention relates to a pharmaceutical composition, particularly an agent for inhibiting matrix metalloproteinase, containing the chromone derivative of the formula (I) or a pharmaceutically acceptable salt thereof.

DESCRIPTION OF THE PREFERRED EMBODIMENTS

Figure 1:
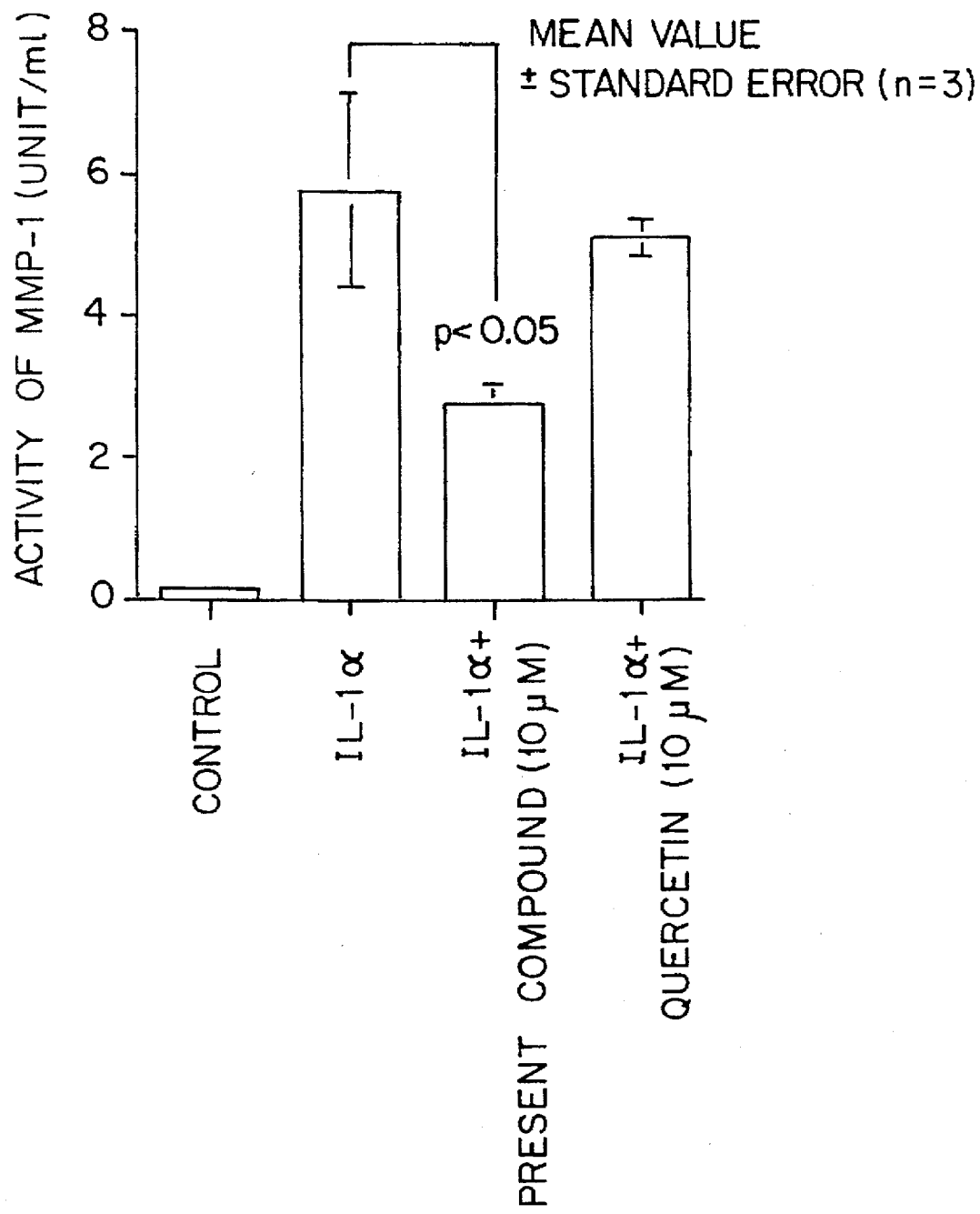
FIG. 1 illustrates an inhibitory activity to interstitial collagenase (MMP-1) in a rabbit cartilage organ culture; see Example 38.

The term "residue of a nitrogen-containing heterocyclic compound" used herein for $R^1$ means a residue of a 5- or 6-membered heteromonocyclic compound having 1 to 4 nitrogen atoms, or a residue of a condensed heterocyclic compound of the above heteromonocyclic compound and a benzene ring, unless otherwise indicated.

The compound of the formula (I) is a compound having a chromone skeleton when X is an oxygen, or a compound having a thiochromone skeleton when X is a sulfur. The compound of the formula (I) wherein X is a sulfur is preferable from a pharmacological standpoint.

In the formula (I), $R^{11}$ is a residue of a nitrogen-containing heterocyclic compound selected from the group consisting of a pyrazolyl, pyrrolyl, triazolyl, benzotriazolyl, benzimidazolyl, indazolyl, and indolyl group, preferably, a pyrazolyl, pyrrolyl, triazolyl, benzotriazolyl, indazolyl, and indolyl group. The triazolyl may be 1,2,4-triazolyl or 1,2,3-triazolyl, but 1,2,4-triazolyl is preferable. The benzotriazolyl may be 1,2,3-benzotriazolyl.

When the residue of the nitrogen-containing heterocyclic compound as $R^{11}$ in the compound of the formula (I) according to the present invention includes a nitrogen atom, the compound of the formula (I) has a structure wherein the nitrogen atom binds to the carbon atom in 2- or 3-position in the chromone or thiochromone skeleton. When the residue of the nitrogen-containing heterocyclic compound as $R^{11}$ in the compound of the formula (I) includes two or more nitrogen atoms, the compound of the formula (I) has a structure wherein the nitrogen atom preferably at 1-position in the residue binds to the carbon atom in 2- or 3-position in the chromone or thiochromone skeleton.

The halogen atom as $R^2$, $R^3$, $R^4$, or $R^5$ may be fluorine, chlorine, bromine, or iodine, preferably fluorine or chlorine.

The alkoxy group or the alkoxy group substituted with one or more alkoxy groups as $R^2$, $R^3$, $R^4$, or $R^5$ is preferably a linear or branched aliphatic alkoxy having 1 to 6 carbon atoms, more preferably ethoxy or methoxy, most preferably methoxy.

The chromone compound of the present invention is preferably the compound of the formula (I) wherein $R^{11}$ is a pyrazolyl, pyrrolyl, triazolyl, benzotriazolyl, benzimidazolyl, indazolyl, or indolyl group, $R^2$ is hydrogen or a lower alkoxy group having 1 to 3 carbon atoms, $R^3$ is hydrogen or halogen, $R^4$ is hydrogen, a lower alkoxy group having 1 to 3 carbon atoms, or a lower alkoxy group having 1 to 3 carbon atoms substituted with a lower alkoxy group having 1 to 3 carbon atoms, $R^5$ is hydrogen, and X is an oxygen or sulfur atom.

The chromone compound of the present invention is more preferably the compound of the formula (I) wherein $R^{11}$ is a pyrazolyl, pyrrolyl, triazolyl, benzotriazolyl, benzimidazolyl, indazolyl, or indolyl group, $R^2$ is hydrogen or methoxy, $R^3$ is hydrogen or chlorine, $R^4$ is hydrogen, methoxy, or methoxymethoxy, $R^5$ is hydrogen, and X is an oxygen or sulfur atom.

Examples of the compound according to the present invention are as follows:

2-pyrrolylchromone,
2-pyrrolylthiochromone,
2-pyrazolylchromone,
2-pyrazolylthiochromone,
2-pyrazolyl-6-chlorochromone,
2-pyrazolyl-6-chlorothiochromone,
2-pyrazolyl-7-methoxychromone,
2-pyrazolyl-7-methoxythiochromone,
2-pyrazolyl-7-(methoxymethoxy) chromone,
2-pyrazolyl-7-(methoxymethoxy) thiochromone,
2-pyrazolyl-5,7-dimethoxychromone,
2-pyrazolyl-5,7-dimethoxythiochromone,
2-(1,2,4-triazolyl) chromone,
2-(1,2,4-triazolyl) thiochromone,
2-(1,2,4-triazolyl)-5,7-dimethoxychromone,
2-(1,2,4-triazolyl)-5,7-dimethoxythiochromone,
2-(1,2,3-benzotriazolyl) chromone,
2-(1,2,3-benzotriazolyl)thiochromone,
2-benzimidazolylchromone,
2-benzimidazolylthiochromone,
2-benzimidazolyl-6-chlorochromone,
2-benzimidazolyl-6-chlorothiochromone,
2-benzimidazolyl-7-methoxychromone,
2-benzmmmmdazolyl-7-methoxythiochromone,
2-benzimidazolyl-5,7-dimethoxychromone,
2-benzimidazolyl-5,7-dimethoxythiochromone,
2-benzimidazolyl-7-(methoxymethoxy) chromone,
2-benzimidazolyl-7-(methoxymethoxy) thiochromone,
2-indazolylchromone,
2-indazolylthiochromone,
2-indazolyl-7-methoxychromone,
2-indazolyl-7-methoxythiochromone,
2-indazolyl-5,7-dimethoxychromone,
2-indazolyl-5,7-dimethoxythiochromone,
2-indolylchromone,
2-indolylthiochromone,
3-pyrrolylchromone,
3-pyrrolylthiochromone,
3-pyrazolylchromone,
3-pyrazolylthiochromone,
3-pyrazolyl-6-chlorochromone,
3-pyrazolyl-6-chlorothiochromone,
3-pyrazolyl-7-methoxychromone,
3-pyrazolyl-7-methoxythiochromone,
3-pyrazolyl-7-(methoxymethoxy) chromone, 3-pyrazolyl-7-(methoxymethoxy) thiochromone,
3-pyrazolyl-5,7-dimethoxychromone,
3-pyrazolyl-5,7-dimethoxythiochromone,
3-(1,2,4-triazolyl) chromone,
3-(1,2,4-triazolyl) thiochromone,
3-(1,2,4-triazolyl)-5,7-dimethoxychromone,
3-(1,2,4-triazolyl)-5,7-dimethoxythiochromone,
3-(1,2,3-benzotriazolyl) chromone,
3-(1,2,3-benzotriazolyl) thiochromone,
3-benzimidazolylchromone,
3-benzimidazolylthiochromone,
3-benzimidazolyl-6-chlorochromone,
3-benzimidazolyl-6-chlorothiochromone,
3-benzimidazolyl-7-methoxychromone,
3-benzimidazolyl-7-methoxythiochromone,
3-benzimidazolyl-5,7-dimethoxychromone,
3-benzimidazolyl-5,7-dimethoxythiochromone,
3-benzimidazolyl-7-(methoxymethoxy) chromone,
3-benzimidazolyl-7-(methoxymethoxy) thiochromone,
3-indazolylchromone,
3-indazolylthiochromone,
3-indazolyl-7-methoxychromone,
3-indazolyl-7-methoxythiochromone,
3-indazolyl-5,7-dimethoxychromone,
3-indazolyl-5,7-dimethoxythiochromone,
3-indolylchromone,
3-indolylthiochromone, The salt of the chromone derivative of the present invention is formed at $R^{11}$, the residue of the nitrogen-containing heterocyclic compound. The salt may be, for example, an acid addition salt of an inorganic or organic acid, preferably the pharmaceutically acceptable salt. As the acid addition salt, there may be mentioned, for example, hydrochloride, sulfate, methanesulfonate, or p-toluenesulfonate; a salt of a dicarboxylic acid, such as oxalate, malonate, succinate, maleate, or fumarate; or a salt of a monocarboxylic acid, such as acetate, propionate, or butyrate.

The chromone derivative of the formula (I) according to the present invention wherein $R^{11}$ binds to the carbon atom in 2-position of the chromone or thiochromone skeleton may be prepared by, for example, a process developed by the inventors of the present invention. More particularly, the chromone derivative of the formula (IA) may be prepared by reacting the compound of the formula (II) wherein a halogen atom binds to carbon atom at 3-position of the chromone or thiochromone skeleton and the compound of the formula (III) in the presence of a base. If the starting compound of the formula (III) wherein $R^1$ is $R^{11}$ is used in the above process, the chromone derivative of the formula (I) according to the present invention wherein $R^{11}$ binds to the carbon atom in 2-position of the chromone or thiochromone skeleton can be prepared.

Hitherto, when an imidazolyl group was introduced into the carbon atom at 2-position of the chromone skeleton, the Michael reaction using 3-bromochromone and a silver salt of imidazole was known (P. Cozzi et al., J. Heterocycl. Chem. (1985) Vol. 22, No. 2, pp. 441–443). On the contrary, ease of procedure, easier availability of reagents and better yield can be achievedby conducting the reaction in the presence of a base according to the process of the present invention.

In the compound of the formula (II), the halogen atom at 3-position in the chromone or thiochromone skeleton may be chlorine, bromine or iodine, but iodine or bromine are preferable in view of the yield. More particularly, in the compound of the formula (II), when X is oxygen, the halogen is preferably iodine, or when X is sulfur, the halogen is preferably bromine. The base which can be used is, for example, an ordinary inorganic or organic base, but a weak base is preferable. As the weak base, a carbonate or hydrogen carbonate of an alkali metal, such as lithium, potassium, sodium or cesium, is more preferable, but potassium carbonate is most preferable. It is preferable in the process of the present invention to carry out the reaction, for example, in an organic solvent, such as dimethylformamide, at 20° to 150° C. for 1 to 100 hours.

The chromone derivative of the formula (I) according to the present invention wherein $R^{11}$ binds to the carbon atom in 3-position of the chromone or thiochromone skeleton may be prepared by, for example, a process developed by the inventors of the present invention. More particularly, the chromone derivative of the formula (IB) may be prepared by reacting the compound of the formula (IV) and the compound of the formula (III) in the presence of a base. If the starting compound of the formula (III) wherein $R^1$ is $R^{11}$ is used in the above process, the chromone derivative of the formula (I) according to the present invention wherein $R^{11}$ binds to the carbon atom in 3-position of the chromone or thiochromone skeleton can be prepared.

An inorganic or organic base may be used as the base. Examples of the base are potassium hydroxide, potassium carbonate, 1,8-diazabicyclo[5.4.0]-7-undecene (hereinafter referred to as "DBU"), or N,N-diisopropylethylamine. A weak base, such as potassium carbonate, DBU, or N,N-diisopropylethylamine, is preferable, but DBU is more preferable. It is preferable in the process of the present invention to carry out the reaction, for example, in an organic solvent, such as acetonitrile, at 0° to 50° C. for 1 to 120 minutes. When DBU is used as the base, the reaction is preferably carried out at room temperature for 1 to 20 minutes.

The chromone derivative of the present invention or a salt thereof may be converted from a free derivative to a salt, from a salt to a different salt, or from a salt to a free derivative, according to methods which are known. For example, a free chromone derivative may be reacted with an equivalent amount of an inorganic acid, such as hydrochloric or sulfuric acid, or an organic acid, such as malic, citric or acetic acid, to obtain a corresponding acid addition salt. The resulting salt can be reacted with an alkali hydroxide, such as sodium or potassium hydroxide, to obtain a free chromone derivative. The salt is soluble in water. But the free chromone derivative is sparingly soluble in water, and can be isolated by precipitation.

The reaction product obtainedby the process as above may be purified by, for example, extraction, chromatography, crystallization and/or reprecipitation. The structure of the purified compound may be confirmed by, for example, infrared absorption spectrum, ultraviolet absorption spectrum, nuclear magnetic resonance spectrum, elemental analysis, and/or mass spectrum.

The toxicity of the chromone derivatives of the present invention was examined. An amount of 500 mg/kg (weight) of 2-benzimidazolyl-5,7-dimethoxychromone, as a typical example of the present derivatives was administered orally to male mice and male rats which were then observed for seven days. No deaths and no remarkable toxicity were observed. The chromone derivatives of the present invention are extremely safe compounds (see Example 37).

The chromone derivative of the present invention exhibits, as a pharmacological effect, the function to inhibit matrix metalloproteinases (see Examples 38 and 39).

The chromone derivative of the present invention exhibits an antitumor activity (see Example 40).

Accordingly, the chromone derivatives of the present invention or pharmaceutically acceptable salts thereof are useful as effective ingredients of matrix metalloproteinase inhibitors for treating various types of diseases accompanying the matrix decomposition, by virtue of the function to inhibit production of matrix metalloproteinases. Examples of such various types of diseases accompanying the matrix decomposition are arthropathy, such as rheumatoid arthritis, osteoarthritis, periarthritis humeroscapularis, shoulder-arm-neck syndrome, lumbago, or the like, corneal ulcer, wound, granuloma, periodontitis, vesicular exanthem, glomerular nephritis, pulmonary emphysema, bone resorption, infiltration and metastasis of cancer, or the like.

The pharmaceutical composition containing as an effective ingredient the chromone derivative of the present invention or pharmaceutically acceptable salts thereof, particularly the matrix metalloproteinase inhibitors, may be in the form of any conventional formulation. The pharmaceutical composition may contain the derivative alone, or a mixture of the derivative with any pharmaceutically acceptable carrier or diluent. The amount of the effective ingredient contained in the composition is not particularly limited, but may for example be 0.01 to 100% by weight, preferably 0.1 to 70% by weight.

The pharmaceutical composition, in particular the matrix metalloproteinase inhibitor, of the present invention may be administered orally or parenterally. The composition may be formulated into any forms suitable therefor. The oral administration includes sublingual administration, and the parenteral administration includes subcutaneous, intramuscular, or intra-cavitas-articular administration, or intravenous administration by injection or dripping, or percutaneous administration. The matrix metalloproteinase inhibitor of the present invention may be administered as various formulations, and may be in various forms, such as powder, granule, tablet, sugar-coated tablet, capsule, suppository, suspension, solution, emulsion, injectionable liquid, or ointment, so long as they contain an effective amount of the active ingredient. Therefore, it is to be understood that the pharmaceutical composition of the present invention may be prepared, using any known conventional methods for formulation.

The dose of the pharmaceutical composition, in particular the matrix metalloproteinase inhibitor, of the present invention varies with the patient (mammal, particularly human), age, individual differences, and/or symptom, and thus is not limited. Generally speaking, however, when a human is treated, the dose of oral administration of the chromone derivative of the present invention is in the range of 0.1 to 500 mg/kg (body weight), preferably 0.5 to 200 mg/kg (body weight) per day. The dose for injection of the chromone derivative of the present invention may be in the range of 0.001 to 20 mg/kg (body weight) per day. The dose may be usually divided into 1 to 4 dosages in a day.

The chromone derivatives of the present invention are useful for treating various types of diseases relating to the matrix metalloproteinase, because of the function to inhibit production of matrix metalloproteinases.

There are various types of arthropathy, for example, rheumatoid arthritis and osteoarthritis. Although there are considerable differences of the causes and conditions between rheumatoid arthritis and osteoarthritis, the articular function becomes eventually obstructed by the destruction of the cartilage in both of rheumatoid arthritis and osteoarthritis. Accordingly, if the destruction of the cartilage or the tissue may be depressed, symptoms will be improved.

The articular cartilage is composed of chondrocytes and the cartilage matrix. The cartilage matrix has a three-dimensional structure which is formed by non-covalently binding the type II collagen (the fibrous protein produced by the chondrocytes) and the proteoglycan (glycoprotein complex), with hyaluronic acid whereby they are complicatedly entangled. The matrix holds a large amount of water, which enables the normal articular functions to be maintained. The main polysaccharide constituting the proteoglycan is glycosaminoglycan (hereinafter referred to as GAG), which is composed of chondroitin sulfate and keratan sulfate. It is known that the production and release of the matrix proteinases, such as collagenase, gelatinase, stromelysin, or matrilysin, are increased and the destruction of the matrix are increased in rheumatoid arthritis, osteoarthritis, or the like. Accordingly, the matrix metalloproteinase inhibitors of the present invention is effective in the treatment of the diseases.

Metastatic cancer cells have not only the basic abilities of tumor cells, such as abnormal proliferation potency and inducibility of vascularization, or evasion from immune response, but also the abilities for abnormal motility and adhesion properties, production of extracellular matrix proteinases, proliferation in infiltration and metastasis location, vascularization, and the like. It has become clear that extracellular proteinases positively take part in processes of infiltration, proliferation, vascularization, and the like. Therefore, a compound which may suppress production, secretion, or activation of the extracellular matrix proteinase would be useful for prevention of cancer metastasis and inhibition of cancer growth.

EXAMPLES

The present invention will now be further illustrated by, but is by no means limited to, the following Examples:

Example 1: Preparation of 3-iodochromone

2-Hydroxyacetophenone (13.6 g) and N,N-dimethylformamide dimethylacetal (7.8 g) were reacted at 90° to 100° C. for 2.5 hours. The reaction mixture was concentrated under reduced pressure, and the residue was recrystallized from benzene/n-hexane to give 3-(N,N-dimethylamino)-1-(2-hydroxyphenyl) propenone (melting point=135°–138° C.; 17.8 g, yield=93%) as a yellow compound.

The resulting propenone compound (19.1 g) was dissolved in chloroform (100 ml). Iodine (38 g) was portionwise added and the whole was stirred at room temperature for 10 hours. The reaction mixture was washed with 5% aqueous solution of sodium thiosulfate and then with purified water. The organic layer was dried over anhydrous sodium sulfate, and concentrated under reduced pressure. The residue was purified by silica gel column chromatography (ethyl acetate/n-hexane=1:3) to obtain the titled compound (melting point=95°–97° C.; 15.8 g; yield=82 %) as crystals.

Example 2: Preparation of 2-pyrazolylchromone

To an eggplant type flask (20 ml), 3-iodochromone (136 mg) prepared in Example 1, pyrazole (136 mg), potassium carbonate (1382 mg), and dimethylformamide (15 ml) were added and the mixture was reacted at 80° C. for 20 hours with stirring. The reaction mixture was added to ice water and extracted with chloroform. The organic layer was separated, dried over anhydrous sodium sulfate, and concentrated under reduced pressure. The residue was purifiedby the silica gel column chromatography, and the purified compound was recrystallized from benzene/hexane to give the titled compound (75.1 mg; yield=70.8%) as white needle crystals. Melting point: 143°–144° C. $^1$H-NMR (CDCl$_3$, δ ppm): 6.90 (s, H3), 8.24 (dd, H5), 7.46–7.58 (m, H6), 7.76 (t, H7), 7.46–7.58 (m ,H8), 7.85 (d, H3'), 6.59 (dd, H4'), 8.23 (d, H5').

Example 3: Preparation of 3-pyrrolylchromone

To an eggplant type flask (25 ml), 3-iodochromone (136 mg) prepared in Example 1, pyrrol (134 mg), potassium carbonate (1382 mg), and dimethylformamide (15 ml) were added and the mixture was reacted at 80° C. for 20 hours with stirring. The reaction mixture was added to ice water and extracted with chloroform. The organic layer was dried over anhydrous sodium sulfate, and concentrated under reduced pressure. The residue was purified by the silica gel column chromatography, and the purified product was recrystallized from benzene/hexane to give the titled compound (59.9 mg; yield=56.4%) as light ocher crystals. Melting point: 134°–135 ° C. $^1$H-NMR(CDCl$_3$, δ ppm): 6.31 (s ,H3), 8.22 (dd, H5), 7.41–7.54 (m, H6), 7.70 (t, H7), 7.41–7.54 (m, H8), 7.32 (br. t, H2'), 6.44(br. t, H3'), 6.44(br. t, H4'), 7.32(br. t, H5').

Example 4: Preparation of 2-(1,2,4-triazolyl) chromone

To an eggplant type flask (25 ml), 3-iodochromone (136 mg) prepared in Example 1, 1,2,4-triazole (138 mg), potassium carbonate (1382 mg), and dimethylformamide (15 ml) were added and the mixture was reacted at 80° C. for 2 hours with stirring. The reaction mixture was added to ice water and extracted with chloroform. The organic layer was dried over anhydrous sodium sulfate, and concentrated under reduced pressure. The residue was purifiedby the silica gel column chromatography, and the purified compound was recrystallized from benzene/hexane to give the titled compound (68 mg; yield =63.8%) as white needle crystals. Melting point: 210° C. $^1$H-NMR(CDCl$_3$, δ ppm): 6.90 (s, H3), 8.26 (dd, H5), 7.47–7.60 (m, H6), 7.77 (t, H7), 7.47–7.60 (m, H8), 8.19 (s, H3'), 8.91 (s, H5').

Example 5: Preparation of 2-benzimidazolylchromone

To an eggplant type flask (25 ml), 3-iodochromone (136 mg) prepared in Example 1, benzimidazole (236 mg), potassium carbonate (1382 mg), and dimethylformamide (15 ml) were added and the mixture was reacted at 80° C. for 2 hours with stirring. The reaction mixture was added to ice water and extracted with chloroform. The organic layer was dried over anhydrous sodium sulfate, and concentrated under reduced pressure. The residue was purifiedby the silica gel column chromatography, and the purified compound was recrystallized from benzene/hexane to give the titled compound (114.5 mg; yield=87.0 %) as white needle crystals. Melting point: 232° C. $^1$H-NMR(CDCl$_3$, δ ppm): 6.59 (s, H3), 8.28 (dd, H5), 7.48–7.64 (m, H6), 7.78 (t, H7), 7.48–7.64 (m, H8), 8.48 (s, H2'), 7.86–7.94 (m, H4'), 7.45–7.50 (m, H5'), 7.45–7.50 (m, H6'), 7.86–7.94 (m, H7').

Example 6: Preparation of 2-indazolylchromone

To an eggplant type flask (25 ml), 3-iodochromone (136 mg) prepared in Example 1, indazole (236 mg), potassium carbonate (1382 mg), and dimethylformamide (15 mg) were added and the mixture was reacted at 80° C. for 30 hours with stirring. The reaction mixture was added to ice water and extracted with chloroform. The organic layer was dried over anhydrous sodium sulfate, and concentrated under reduced pressure. The residue was purifiedby the silica gel column chromatography, and the purified product was recrystallized from benzene/hexane to give the titled compound (113.6 mg; yield=88.5%) as crystals. Melting point: 237°–238° C. $^1$H-NMR(CDCl$_3$, δ ppm): 6.94 (s, H3), 8.26 (dd, H5), 7.58–7.68 (m, H6), 7.75 (t, H7), 7.58–7.68 (m, H8), 8.30 (s, H3'), 7.82 (m, H4'), 7.35–7.53 (m, H5'), 7.35–7.53 (m, H6'), 8.26 (m, H7') .

Example 7: Preparation of 2-indolylchromone

To an eggplant type flask (25 ml), 3-iodochromone (136 mg) prepared in Example 1, indole (234 mg), potassium carbonate (1382 mg), and dimethylformamide (15 mg) were added and the mixture was reacted at 80° C. for 30 hours with stirring. The reaction mixture was added to ice water and extracted with chloroform. The organic layer was dried over anhydrous sodium sulfate, and concentrated under reduced pressure. The residue was purifiedby the silica gel column ghromatography, and the purified product was recrystallized from benzene/hexane to give the titled compound (42.3 mg; yield=32.2%) as crystals. Melting point: 157°–158° C. $^1$H-NMR(CDCl$_3$, δ ppm): 6.46 (s, H3), 8.26 (dd, H5), 7.47 (t, H6), 7.72 (t, H7), 7.58 (d, H8), 7.55 (d, H2'), 6.80 (d, H3'), 7.66 (d, H4'), 7.28–7.42 (m, H5'), 7.28–7.42 (m, H6'), 7.99 (m, H7').

Example 8: Preparation of 3-bromothiochromone

Thiophenol (22 g) was reacted with acrylic acid (7.2 g) at 100° C. for 20 hours. The reaction mixture was dissolved in saturated aqueous solution of sodium hydrogencarbonate (150 ml), and the unreacted thiophenol was extracted with chloroform (30 ml×3). The sodium hydrogencarbonate layer was acidified with 10% hydrochloric acid to precipitate crystals. The resulting crystals were recrystallized from ether/n-hexane to give 3-phenylthiopropionic acid (melting point=60° C.; 9.2 g).

Then, 3-phenylthiopropionic acid (8.8 g) was reacted with polyphosphoric acid (88 g) at 80 ° C for 8 hours. The reaction mixture was added to ice water, and extracted with methylene chloride three times. The organic layer was dried over anhydrous sodium sulfate and concentrated under reduced pressure. The residue was evaporated under reduced pressure to give 2,3-dihydrothiochromone (boiling point= 110°–115° C./3 mmHg; 5.9 g).

Thereafter, 2,3-dihydrothiochromone (1 g) was dissolved in chloroform (10 ml), and a solution of bromine (2 g) in chloroform (10 ml) was gradually added thereto under sunlight. After the color of bromine disappeared, the solvent was evaporated. The residue was recrystallized from methanol to obtain 3,3-dibromo-2,3-dihydrothiochromone (melting point=96° C.; 1.8 g).

Then, 3,3-dibromo-2,3-dihydrothiochromone (1 g) was added to pyridine (5 ml) and dissolved therein by heating. The solution was further heated in water bath for 10 minutes. The reaction mixture was added to ice water. The precipitated crystals were collected by filtration and recrystallized from benzene to obtain the titled compound (melting point= 41° C.; 1.8 g) as yellow needle crystals.

Example 9: Preparation of 2-pyrazolylthiochromone

To an eggplant type flask (25 ml), 3-bromothiochromone (121 mg) prepared in Example 8, pyrazole (136 mg), potassium carbonate (1382 mg), and dimethylformamide (15 ml) were added. The mixture was reacted at 80° C. for 20 hours with stirring. The reaction mixture was added to ice water and extracted with chloroform. The organic layer was dried over anhydrous sodium sulfate, and concentrated under reduced pressure. The residue was purified by the silica gel column chromatography and recrystallized from benzene/hexane to give the titled compound (90.5 mg; yield=84.6%) as white needle crystals. Melting point: 189° C. $^1$H-NMR (CDCl$_3$, δ ppm): 7.16 (s, H3), 8.50 (d, H5), 7.52–7.60 (m, H6), 7.66 (t, H7), 7.52 (m, H8), 7.82 (d, H3'), 6.60 (dd, H4'), 8.08 (d, H5').

Example 10: Preparation of 2-pyrrolylthiochromone

To an eggplant type flask (25 ml), 3-bromothiochromone (121 mg) prepared in Example 8, pyrrole (134 mg), potassium carbonate (1382 mg), and dimethylformamide (15 ml) were added. The mixture was reacted at 80° C. for 20 hours with stirring. The reaction mixture was added to ice water and extracted with chloroform. The organic layer was dried over anhydrous sodium sulfate, and concentrated under reduced pressure. The residue was purified by the silica gel column chromatography and the purified product was recrystallized from benzene/hexane to give the titled compound (57.5 mg; yield=54.0%) as ocher crystals. Melting point: 135°–136° C. $^1$H-NMR(CDCl$_3$, δ ppm): 7.02 (s, H3), 8.51 (dd, H5), 7.56 (t, H6), 7.61–7.68 (m, H7), 7.61–7.68 (m, H8), 7.22 (br. t, H2'), 6.44 (br. t, H3'), 6.44 (br. t, H4'), 7.22 (br. t, H5').

Example 11: Preparation of 2-(1,2,4-triazolyl)thiochromone

To an eggplant type flask (25 ml), 3-bromothiochromone (121 mg) prepared in Example 8, 1,2,4-triazole (138 mg), potassium carbonate (1382 mg), and dimethylformamide (15 ml) were added. The mixture was reacted at 80° C. for 20 hours with stirring. The reaction mixture was added to ice water and extracted with chloroform. The organic layer was dried over anhydrous sodium sulfate, and concentrated under reduced pressure. The residue was purified by the silica gel column chromatography and recrystallized from benzene/hexane to give the titled compound (92.6 mg; yield=80.8%) as white needle crystals. Melting point: 232° C. $^1$H-NMR(DMSO-d$_6$, δ ppm): 7.70 (s, H3), 8.35 (dd, H5), 7.66 (t, H6), 7.80 (t, H7), 7.99 (d, H8), 8.40 (s, H3'), 9.63 (s, H5').

Example 12: Preparation of 2-benzimidazolylthiochromone

To an eggplant type flask (25 ml), 3-bromothiochromone (121 mg) prepared in Example 8, bezimidazole (236 mg), potassium carbonate (1382 mg), and dimethylformamide (15 ml) were added. The mixture was reacted at 80° C. for 20 hours with stirring. The reaction mixture was added to ice water and extracted with chloroform. The organic layer was dried over anhydrous sodium sulfate, and concentrated under reduced pressure. The residue was purified by the silica gel column chromatography and recrystallized from benzene/hexane to give the titled compound (133 mg; yield=95.3%) as white needle crystals. Melting point: 160°–161° C. $^1$H-NMR(CDCl$_3$, δ ppm): 7.22 (s, H3), 8.59 (d, H5), 7.64 (t, H6), 7.73 (t, H7), 7.70 (m, H8), 8.25 (s, H2'), 7.78–7.93 (m, H4'), 7.40–7.48 (m, H5'), 7.40–7.48 (m, H6'), 7.78–7.93 (m, H7').

Example 13: Preparation of 2-imidazolylthiochromone

To an eggplant type flask (25 ml), 3-bromothiochromone (121 mg) prepared in Example 8, indazole (236 mg), potassium carbonate (1382 mg), and dimethylformamide (15 ml) were added. The mixture was reacted at 80° C. for 20 hours with stirring. The reaction mixture was added to ice water and extracted with chloroform. The organic layer was dried over anhydrous sodium sulfate, and concentrated under reduced pressure. The residue was purified by the silica gel column chromatography and recrystallized from benzene/hexane to give the titled compound (112.5 mg; yield=85.5%) as crystals. Melting point: 187°–188° C. $^1$H-NMR(CDCl$_3$, δ ppm): 7.42 (s, H3), 8.54 (d, H5), 7.52–7.70 (m, H6), 7.52–7.70 (m, H7), 7.52–7.70 (m, H8), 8.31 (s, H3'), 7.85 (d, H4'), 7.35–7.62 (m, H5'), 7.35–7.62 (m, H6'), 8.08 (d, H7')

Example 14: Preparation of 2-indolylthiochromone

To an eggplant type flask (25 ml), 3-bromothiochromone (121 mg) prepared in Example 8, indole (234 mg), potassium carbonate (1382 mg), and dimethylformamide (15 ml) were added. The mixture was reacted at 80° C. for 20 hours with stirring. The reaction mixture was added to ice water and extracted with chloroform. The organic layer was dried over anhydrous sodium sulfate, and concentrated under reduced pressure. The residue was purified by the silica gel column chromatography and recrystallized from benzene/hexane to give the titled compound (118.5 mg; yield=40.4%) as crystals. Melting point: 155°–156° C. $^1$H-NMR(CDCl$_3$, δ ppm): 7.22 (s, H3), 8.57 (d, H5), 7.55–7.72 (m, H6), 7.55–7.72 (m, H7), 7.55–7.72 (m, H8), 7.45 (d, H2'), 6.79 (d, H3'), 7.60–7.70 (m, H4'), 7.22–7.38 (m, H5'), 7.22–7.38 (m, H6'), 7.88 (d, H7').

Example 15: Preparation of 3-(dimethylamino)-4',6'-dimethoxy-2'-hydroxyacrylophenone To an eggplant type flask (100 ml), 4,6-dimethoxy-2-hydroxyacetophenone (9.40 g) and N,N-dimethylformamide dimethylacetal (9.02 g) were added, and the mixture was reacted at 100° C. for 2.5 hours under argon atmosphere. The reaction mixture was concentrated under reduced pressure to obtain orange crystals (11.74 g). The crystals were recrystallized from benzene/n-hexane to give the titled compound (10.84 g; yield=86.3%) as yellow crystals. Melting point: 146°–147° C. $^1$H-NMR(CDCl$_3$, δ ppm): 2.92 (br, 3H, N-Me), 3.13 (br, 3H, N-Me), 3.79 (s, 3H, OMe), 3.83 (s, 3H, OMe), 5.90 (s, 1H, Ar-H), 6.07 (s, 1H, Ar-H), 6.25 (d, 1H, COH), 7.92 (d, 1H, CHN).

Example 16: Preparation of 5,7-dimethoxy-3-iodochromone

To an eggplant type flask (500 ml), 3-dimethylamino-4',6'-dimethoxy-2'-hydroxyacrylophenone (5.026 g) prepared in Example 15 and methyl alcohol (200 ml) were added. The mixture was dissolved by heating at 80° C. for 10 minutes with stirring. After the solution was cooled, iodine (10.152 g) was slowly added. After 15 minutes, the disappearance of the starting material was confirmed by thin layer chromatography. To the reaction mixture, methylene chloride (700 ml) and then 5% aqueous solution of sodium thiosulfate (200 ml) were added to reduce iodine. The organic layer was separated, and washed with distilled water (100 ml). The organic layer was dried over anhydrous sodium sulfate and concentrated under reduced pressure. The crude product was separated and purified by silica gel column chromatography (n-hexane/ethyl acetate=2/1 to 1/2), and recrystallized from ether to give the titled compound (3.43 g; yield=34.5%) as colorless crystals. Melting point: 158°–160° C. $^1$H-NMR (CDCl$_3$, δ ppm): 3.88 (s, 3H, OMe), 3.93 (s, 3H, OMe), 6.38 (s, 1H, ArH), 6.42 (s, 1H, ArH), 8.06 (s, 1H, H2).

Example 17: Preparation of 2-benzimidazolyl-5,7-dimethoxychromone

A mixture of 5,7-dimethoxy-3-iodochromone (166 mg) prepared in Example 16, benzimidazole (236 mg), potassium carbonate (1382 mg), and dimethylformamide (15 ml) was reacted at 80° C. for 2 hours with stirring. The reaction mixture was added to ice water and extracted from chloroform. The organic layer was dried over anhydrous sodium sulfate, and concentrated under reduced pressure. The residue was purifiedby the silica gel column chromatography, and recrystallized from benzene/hexane to give the titled compound (107.9 mg; yield =67.0%) as orange plate crystals. Melting point: 245°–246° C. Mass spectrum (M$^+$): 332. $^1$H-NMR(CDCl$_3$, δ ppm): 6.71 (s, 1H, H3), 6.62 (s, H6), 8.26 (s, H8), 6.43 (s, H3'), 7.80 (d, H4'), 7.58 (t, H5'), 7.34 (t, H6'), 8.11 (d, H7'), 3.96 (s, 3H, 5MeO), 3.97 (s, 3H, 7MeO).

Example 18: Preparation of 2-pyrazolyl-5,7-dimethoxychromone

A mixture of 5,7-dimethoxy-3-iodochromone (166 mg) prepared in Example 16, pyrazole (136 mg), potassium carbonate (1382 mg), and dimethylformamide (15 ml) was reacted at 80° C. for 2 hours-with stirring. The reaction mixture was added to ice water and extracted from chloroform. The organic layer was dried over anhydrous sodium sulfate, and concentrated under reduced pressure. The residue was purified by the silica gel column chromatography, and recrystallized from benzene/hexane to give the titled compound (122 mg; yield=90.0%) as white bulk crystals. Melting point: 197°–198° C. Mass spectrum (M$^+$): 272. $^1$H-NMR(CDCl$_3$, δ ppm): 6.77 (s, 1H, H3), 6.55 (d, 1H, H6), 7.81 (s, 1H, H8), 8.12 (s, 1H, H3'), 6.41 (d, H4'), 6.54 (s, 1H, H5'), 3.96 (s, 3H, 5MeO), 4.06 (s, 3H, 7MeO).

Example 19: Preparation of 2-indazolyl-5,7-dimethoxychromone

A mixture of 5,7-dimethoxy-3-iodochromone (166 mg) prepared in Example 16, indazole (236 mg), potassium carbonate (1382 mg), and dimethylformamide (15 ml) was reacted at 80° C. for 2 hours with stirring. The reaction mixture was added to ice water and extracted from chloroform. The organic layer was dried over anhydrous sodium sulfate, and concentrated under reduced pressure. The residue was purifiedby the silica gel column chromatography, and recrystallized from benzene/hexane to give the titled compound (117 mg; yield=73.0%) as light yellow needle crystals. Melting point: 253°–255° C. Mass spectrum (M$^+$): 332. $^1$H-NMR(CDCl$_3$, δ ppm): 6.62 (s, 1H, H6), 8.26 (s, 1H, H8), 6.71 (s, 1H, H3), 6.43 (s, 1H, H3'), 7.80 (d, 1H, H4'), 7.58 (d, 1H, H5'), 7.34 (t, 1H, H6'), 8.11 (d, 1H, H7'), 3.96 (s, 3H, 5MeO), 3.97 (s, 3H, 7MeO).

Example 20: Preparation of 2-(1,2,4-triazolyl)-5,7-dimethoxychrome

A mixture of 5,7-dimethoxy-3-iodochromone (166 mg) prepared in Example 16, 1,2,4-triazole (138 mg), potassium carbonate (1382 mg), and dimethylformamide (15 ml) was reacted at 80° C. for 2 hours with stirring. The reaction mixture was added to ice water and extracted from chloroform. The organic layer was dried over anhydrous sodium sulfate, and concentrated under reduced pressure. The residue was purified by the silica gel column chromatography, and recrystallized from benzene/hexane to give the titled compound (17.6 mg; yield =13.0%) as yellow needle crystals. Melting point: 258°–260° C. Mass spectrum (M$^+$): 273.

Example 21: Preparation of 7-methoxy-3-iodochromone

The procedure disclosed in Examples 15 and 16 was repeated, except that 4-methoxy-2-hydroxyacetophenone (Tokyo Kasei) (16.7 g) was used instead of 4,6-dimethoxy-2-hydroxyacetoophenone, to obtain the titled compound (24.8 g; yield=82%) as crystals.

Example 22: Preparation of 2-pyrazolyl-7-methoxychromone

A mixture of 7-methoxy-3-iodochromone (151 mg) prepared in Example. 21, pyrazole (136 mg), potassium carbonate (1382 mg), and dimethylformamide (15 ml) was reacted at 80° C. for 2 hours with stirring. The reaction mixture was added to ice water and extracted from chloroform. The organic layer was dried over anhydrous sodium sulfate, and concentrated under reduced pressure. The residue was purifiedby the silica gel column chromatography, and recrystallized from benzene/hexane to give the titled compound (90.8 mg; yield=75.0%) as light yellow needle crystals. Melting point: 170°–171° C. $^1$H-NMR(CDCl$_3$, δ ppm): 3.93 (s, CH$_3$O), 6.56 (hr. s, H3), 8.13 (d, H5), 7.00 (d, H6), 6.94 (d, H8), 6.81 (s, H3'), 7.83 (s, H4'), 8.18 (d, H5').

Example 23: Preparation of 2-benzimidazolyl-7-methoxychromone

A mixture of 7-methoxy-3-iodochromone (151 mg) prepared in Example 21, benzimidazole (236 mg), potassium carbonate (1382 mg), and dimethylformamide (15 ml) was reacted at 80° C. for 2 hours with stirring. The reaction mixture was added to ice water and extracted from chloroform. The organic layer was dried over anhydrous sodium sulfate, and concentrated under reduced pressure. The residue was purifiedby the silica gel column chromatography, and recrystallized from benzene/hexane to give the titled compound (100.2 mg; yield=68.2%) as white needle crystals. Melting point: 201°–203° C. $^1$H-NMR(CDCl$_3$, δ ppm): 3.97 (s, 3H, CH$_3$O), 6.52 (br, 1H, H3), 8.17 (d, 1H, H5'), 7.06 (d, 1H, H6), 6.99 (s, 1H, H8), 8.44 (s, 1H, H2'), 7.85 (d, 1H, H4'), 7.46 (m, H5'), 7.46 (m, 1H, H6'), 7.90 (d ,1H, H7').

Example 24: Preparation of 2-indazolyl-7-methoxychromone

A mixture of 7-methoxy-3-iodochromone (151 mg) prepared in Example 21, indazole (236 mg), potassium carbonate (1382 mg), and dimethylformamide (15 ml) was reacted at 80° C. for 2 hours with stirring. The reaction mixture was added to ice water and extracted from chloroform. The organic layer was dried over anhydrous sodium sulfate, and concentrated under reduced pressure. The residue was purified by the silica gel column chromatography, and recrystallized from benzene/hexane to give the titled compound (40.5 mg; yield=27.6%) as golden crystals. Melting point: 218°–220° C. $^1$H-NMR(CDCl$_3$, δ ppm): 3.97 (s, 3H, CH$_3$O), 6.83 (s, 1H, H3), 8.16 (dd, 1H, H5), 7.02 (s, 1H, H6), 7.01 (s, 1H, H8), 8.27 (s, H3'), 7.36 (d, 1H, H4'), 7.06 (d, 1H, H5'), 7.80 (d, 1H, H6').

Example 25: Preparation of 7-methoxymethoxy-3-iodochromone

The procedure disclosed in Examples 15 and 16 was repeated, except that 4-methoxy-2-hydroxyacetophenone (Tokyo Kasei) (19.6 g) was used instead of 4,6-dimethoxy-2-hydroxyacetophenone, to give the titled compound (10.2 g; yield =83%) as reddish yellow crystals.

Example 26: Preparation of 2-pyrazolyl-7-(methoxymethoxy) chrome

A mixture of 7-methoxymethoxy-3-iodochromone (166 mg) prepared in Example 25, pyrazole (136 mg), potassium carbonate (1382 mg), and dimethylformamide (15 ml) was reacted at 80° C. for 2 hours with stirring. The reaction mixture was added to ice water and extracted from chloroform. The organic layer was dried over anhydrous sodium sulfate, and concentrated under reduced pressure. The residue was purified by the silica gel column chromatography, and recrystallized from benzene/hexane to give the titled compound (99.3 mg; yield=61.3%) as white needle crystals. Melting point: 170° C. $^1$H-NMR(CDCl$_3$, δ ppm): 3.53 (s ,3H, CH$_3$O), 5.29 (s, 2H, MeOCH$_2$), 6.57 (br, 1H, H3), 8.15 (d, 1H, H5), 7.09 (d, 1H, H6), 6.83 (s, 1H, H8), 7.11 (s, 1H, H3'), 7.83 (s, 1H, H4'), 8.20 (d, 1H, H5').

Example 27: Preparation of 2-benzimidazolyl-7-(methoxymethoxy) chrome

A mixture of 7-methoxymethoxy-3-iodochromone (166 mg) prepared in Example 25, benzimidazole (236 mg), potassium carbonate (1382 mg), and dimethylformamide (15 ml) was reacted at 80° C. for 2 hours with stirring. The reaction mixture was added to ice water and extracted from chloroform. The organic layer was dried over anhydrous sodium sulfate, and concentrated under reduced pressure. The residue was purified by the silica gel column chromatography, and recrystallized from benzene/hexane to give the titled compound (34.0 mg; yield =21.0%) as light ocher crystals. Melting point: 172°–173° C. $^1$H-NMR (CDCl$_3$, δ ppm): 3.54 (s, 3H, CH$_3$O), 5.32 (s, 2H, MeOCH$_2$O), 6.53 (s, 1H, H3), 8.16 (d, HS), 7.15 (s, 1H, H6), 7.21 (s, 1H, H8), 8.45 (s, 1H, H2'), 7.85 (d, 1H, H4'), 7.47 (m, 1H, H5'), 7.47 (m, 1H, H6'), 7.90 (d ,1H, H7').

Example 28: Preparation of 6-chloro-3-iodochromone

The procedure disclosed in Examples 15 and 16 was repeated, except that 5-chloro-2-hydroxyacetophenone (Tokyo Kasei) (17.5 g) was used instead of 4,6-dimethoxy-2- hydroxyacetophenone, to give the titled compound (9.9 g; yield =65%) as crystals.

Example 29: Preparation of 2-benzimidazolyl-6-chlorochromone

A mixture of 6-chloro-3-iodochromone (153 mg) prepared in Example 28, benzimidazole (236 mg), potassium carbonate (1382 mg), and dimethylformamide (15 ml) was reacted at 80° C. for 2 hours with stirring. The reaction mixture was added to ice water and extracted from chloroform. The organic layer was dried over anhydrous sodium sulfate, and concentrated under reduced pressure. The residue was purifiedby the silica gel column chromatography, and recrystallized from benzene/hexane to give the titled compound (19.3 mg; yield=13.0%) as white crystals. Melting point: 248°–250° C. Mass spectrum (M$^+$): 296.5.

Example 30: Preparation of 2-pyrazolyl-6-chlorochromone

A mixture of 6-chloro-3-iodochromone (153 mg) prepared in Example 28, pyrazole (136 mg), potassium carbonate (1382 mg), and dimethylformamide (15 ml) was reacted at 80° C. for 2 hours with stirring. The reaction mixture was added to ice water and extracted from chloroform. The organic layer was dried over anhydrous sodium sulfate, and concentrated under reduced pressure. The residue was purifiedby the silica gel column chromatography, and recrystallized from benzene/hexane to give the titled compound (41.9 mg; yield=34.0%) as orange crystals. Melting point: 217°–219° C. Mass spectrum (M$^+$): 246.5.

Example 31: Preparation of 2,3-epoxychromone

Chromone (3 g) was dissolved in ether (200 ml) and the solution was cooled to 0° C. in ice water. Then, 30% hydrogen peroxide (15 ml) and Triton B (10 ml) solution were added portionwise. The whole was stirred at 0° C. for 4 hours. After adding ice water, the reaction liquor was extracted with dichloromethane. The organic layer was washed with sodium thiosulfate, dried over anhydrous sodium sulfate, and concentrated under reduced pressure. The residue was fractionatedby silica gel column chromatography (diethyl ether/hexane =1:8) to give the titled compound (2.34 g; yield =75%). Melting point: 66°–67° C. Mass spectrum (M$^+$): 162. $^1$H-NMR(CDCl$_3$, δ ppm): 3.69 (d, 1H, H3), 5.67 (d, 1H, H2), 7.05 (d, 1H, H8), 7.14 (t, 1H, H6), 7.54 (t, 1H, H7), 7.79 (dd, 1H, H5).

Example 32: Preparation of 3-benzimidazolylchromone

Benzimidazole (472 mg) and DBU (608 mg) were dissolved in acetonitrile (20 ml), and stirred at room temperature for 1 hour. To the resulting solution, a solution of 2,3-epoxychromone (162 mg) in dimethylformamide (5 ml) was added dropwise, and the whole was stirred for 5 minutes. After ice water was added, the reaction mixture was extracted with dichloromethane. The organic layer was dried over anhydrous sodium sulfate, and concentrated under reduced pressure. The residue was fractionatedby silica gel column chromatography (ethyl acetate/hexane=1:3) to give the titled compound (122 mg; yield=93%). Melting point: 154° C. Mass spectrum (M$^+$): 262. $^1$H-NMR(CDCl$_3$, δ ppm): 8.21 (s, 1H, H2), 8.33 (dd, 1H, H5), 7.52 (t, 1H, H6), 7.80 (t, 1H, H7), 7.61 (d, 1H, H8), 8.35 (s, 1H, H2'), 7.33 (m, 3H, H4', 5', 6'), 7.86 (d, 1H, H7').

Example 33: Preparation of 3-pyrazolylchromone

The procedure disclosed in Example 32 was repeated, except that pyrazole (136 mg) was used instead of benzimidazole to give the titled compound (82 mg; yield=77%). Melting point: 141°–142° C. Mass spectrum (M$^+$): 212. $^1$H-NMR(CDCl$_3$, δ ppm): 8.79 (s, 1H, H2), 8.35 (dd, 1H, H5), 7.48 (t, 1H, H6), 7.74 (t, 1H, H7), 7.57 (d, 1H, H8), 7.68 (d, 1H, H3'), 6.48 (t, 1H, H4'), 8.61 (dd, 1H, H5').

Example 34: Preparation of 3-(1,2,4-triazolyl) chromone

The procedure disclosed in Example 32 was repeated, except that 1,2,4-triazole (138 mg) was used instead of benzimidazole to give the titled compound (95.9 mg; yield= 90%). Melting point: 160° C. Mass spectrum (M$^+$): 213. $^1$H-NMR(CDCl$_3$, δ ppm): 8.89 (s, 1H, H2), 8.37 (dd, 1H, H5), 7.53 (t, 1H, H6), 7.79 (t, 1H, H7), 7.61 (d, 1H, H8), 8.08 (s, 1H, H3'), 9.42 (s, 1H, H5').

Example 35: 3-indazolylchromone

The procedure disclosed in Example 32 was repeated, except that indazole (236 mg) was used instead of benzimidazole to give the titled compound (92 mg; yield=86%). Melting point: 159°–160° C. Mass spectrum (M$^+$): 262. $^1$H-NMR(CDCl$_3$, δ ppm): 8.40 (s, 1H, H2), 8.37 (dd, 1H, H5), 7.52 (t, 1H, H6), 7.77 (t, 1H, H7), 7.60 (d, 1H, H8), 8.21 (s, 1H, H3'), 7.38–7.42 (m, 2H, H4', 5'), 7.23 (t, 1H, H6'), 7.78 (m, 1H, H7').

Example 36: Preparation of 3-(1,2,3-benzotriazolyl) chromone

The procedure disclosed in Example 32 was repeated, except that 1,2,3-benzotriazole (237 mg) was used instead of benzimidazole to give the titled compound (119 mg; yield= 91%). Melting point: 179°–180° C. Mass spectrum (M$^+$): 263. $^1$H-NMR(CDCl$_3$, δ ppm): 8.55 (s, 1H, H2), 8.39 (dd, 1H, H5), 7.57 (t, 1H, H6), 7.84 (t, 1H, H7), 7.66 (d, 1H, H8), 7.56–7.60 (m, 2H, H4', 5'), 7.44–7.48 (m, 1H, H6'), 7.68 (d, 1H, H7').

Example 37: Acute toxicity of chromone derivative

The acute toxicity of the chromone derivative of the present invention was evaluated, for Crj:CD-1(ICR) mice (male; 6 weeks old) and Wistar rat (male; 6 weeks old). After 2-benzimidazolyl-5,7-dimethoxychromone prepared in Example 17 was administered orally at doses of 500 mg/kg, the conditions of animals were observed for 7 days. No deaths were observed. Further, no change was observed in comparison with the control group in each of the general state and body weight. In the experiments as above, two animals were used for each group.

Example 38: Inhibitory activity to interstitial collagenase

(MMP-1) in rabbit cartilage organ culture

After the articular cartilages were collected from the shoulder and knee of rabbits (New Zealand white; male; 6 weeks old) and divided into small pieces, cultivation experiment was started using Dulbecco's MEM medium containing 0.2% lactoalbumin hydrolysate. The compounds to be tested were dissolved in dimethylsulfoxide (DMSO) and then added to the medium. The concentration of DMSO was 0.25 % by volume with respect to the medium. After 2 hours from addition of the compounds to be tested, 100 units/ml of interleukin-1α (hereinafter referred to as the IL-1α) was added as a stimulant, and the cultivation was performed for 48 hours. Thereafter, the activity of MMP-1 in the supernatant of the culture was measured. Collageno kit (CLN-100) (Collagen-Gijutsu Kensyukai) was used for the measurement of of the activity of MMP-1.

The results are shown as the mean value ± standard error (n=3 per a group). As the chromone derivative of the present invention, 2-benzimidazolyl-5,7-dimethoxychromone prepared in Example 17 was used, and quercetin was used as a comparative compound.

The results are shown in FIG. 1. In the control wherein IL-1α and the compound to be tested were not added, no activity of MMP-1 was observed. When IL-1α was added, the activity of MMP-1 was observed. On the contrary, the chromone derivative of the present invention inhibited the activity of MMP-1 in the culture by inhibiting the production of MMP-1 with comparison with the case where only IL-1α was added.

Example 39: Inhibitory activity to gelatinase A (MMP-2)

production in human fibrosarcoma cells

Human fibrosarcoma cells (HT-1080) were inoculated at the concentration of 1×10$^5$ cells/ml/well to a culture vessel (24 well plate), using RPMI-1640 medium containing 0.2% lactoalbumin hydrolysate. After cultivated for 1 day, the culture liquid was removed, and 1 ml of a fresh RPMI-1640 medium containing 0.2% lactoalbumin hydrolysate. The compounds to be tested were dissolved in DMSO, and then added to the culture liquid. The concentration of DMSO was 0.25% by volume with respect to the medium. After the cultivation was carried out for 3 days from the addition of the compound to be tested, the amount of the MMP-2 in the culture supernatant was determined by a western blotting method using anti-human MMP-2 antibody (Fuji Yakuhin Kogyo) as explained below.

In accordance with the process disclosed in Laemmli, N. K., "Nature", 283: pp. 249–256, 1970, SDS-polyacrylamide gel electrophoresis was carried out, using 5 μl of a sample buffer [a mixture of 2 ml of distilled water, 500 μl of 2 M tris-HCl (pH 6.8), 0.32 g of SDS, 800 μl of β-mercaptoethanol, and 400 μl of 0.05% (w/v) bromophenol blue (Biorad)] and 5 μl of culture. Then, the gel was contacted to a 0.22 μm polyvinylidene fluoride (PVDF) membrane (GVHP Durapore filter; Millipore), and blotting was carried out at room temperature at 160 mA for 18 minutes, using a protein transferring apparatus (MilliBlot-SDS System: Millipore).

After blotting, the PVDF membrane was washed with PBS(-) [KCl=0.2 g/l, KH$_2$PO$_4$=0.2 g/l, NaCl=8 g/l, Na$_2$HPO$_4$ (anhydrous)=1.15 g/l] containing 0.5% Tween 20 by shaking for 5 minutes three times, and then blocked at 37° C. for 1 hour with an aquous solution of 4% non-fat dried milk (Block Ace: Snow Brand Milk). After blocking, the PVDF membrane was washed with PBS(-) containing 0.5% Tween 20 by shaking for 5 minutes three times, and then a first antibody reaction was carried out at 37° C. for 1 hour, using anti-human MMP-2 antibody (Fuji Yakuhin Kogyo) (500 μg/ml) diluted with 500 times its volume of an aqueous solution of 4% non-fat dried milk as a first antibody. After the first antibody reaction was completed, the PVDF membrane was washed with PBS(-) containing 0.5% Tween 20 by shaking for 5 minutes three times.

After the membrane was washed, a second antibody reaction was carried out at 37° C. for 1 hour, using biotinylated anti-mouse IgG antibody (Vector Laboratories) (1 mg/ml) diluted with 1000 times its volume of an aqueous solution of 4% non-fat dried milk. After the second antibody reaction was completed, the PVDF membrane was washed with PBS(-) containing 0.5% Tween 20 for 10 minutes three times.

After the membrane was washed, the reaction was performed at 37° C. for 1 hour, using a solution of streptoavidin horseradish peroxidase (5 mg/ml) (Vector Laboratories) diluted with 2000 times its volume of an aqueous solution of 4% non-fat dried milk.

After the reaction was completed, the PVDF membrane was washed with PBS(-) containing 0.5% Tween 20 by shaking for 5 minutes three times, and then was washed with PBS(-) without 0.5% Tween 20 by shaking for 5 minutes three times.

After excessive PBS(-) solution was removed, a western blotting detection reagent (ECL Western blotting detection reagent: Amersham) was sprinkled over the PVDF membrane, the membrane was allowed to stand at room temperature for 1 minute. Then, excessive detection reagent was removed, and the membrane was wrapped in a film. An X-ray film (Hyperfilm-ECL: Amersham) was contacted to the reaction surface and exposed.

Figure 2:
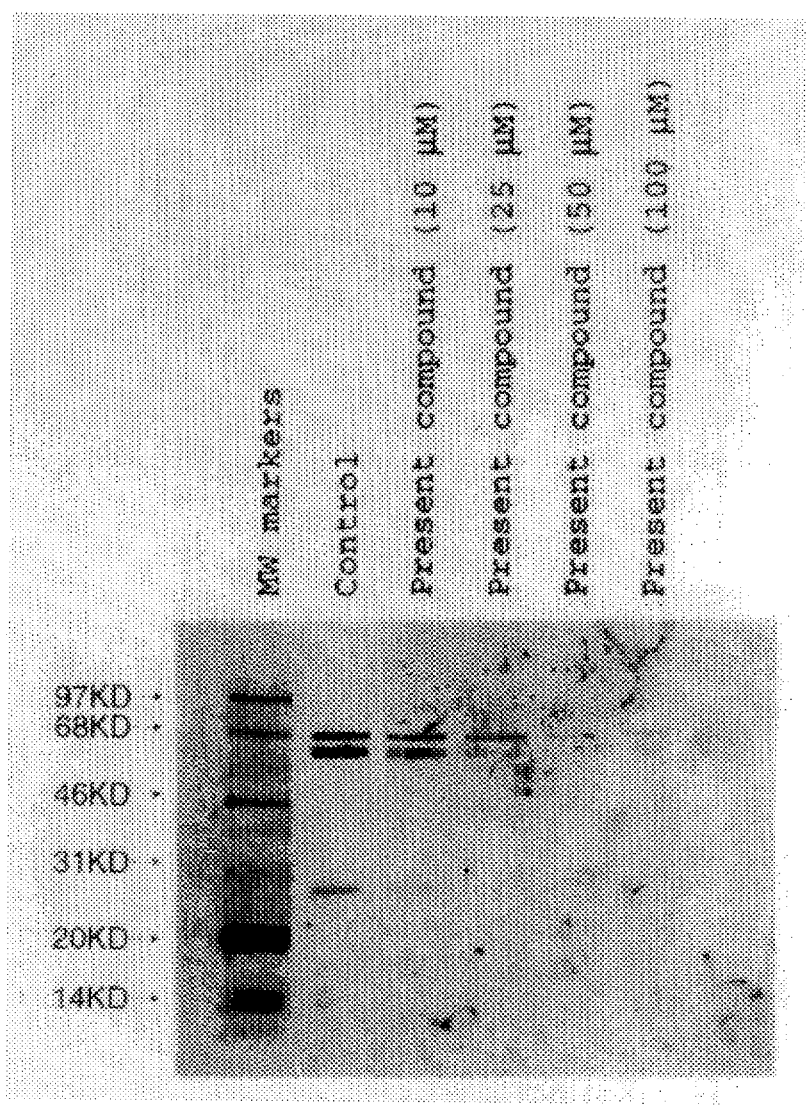
FIG. 2 illustrates the result of the electrophoresis for detecting gelatinase A (MMP-2) by the western blotting method, and showing an inhibihory activity to MMP-2 production in human fibrosarcoma cells; see Example 39.

The result of the electrophoresis for detecting MMP-2 by the western blotting method is shown in FIG. 2. As the compound of the present invention (the present compound), 2-pyrrolylthiochromone prepared in Example 10 was used. In control test, only DMSO was added instead of the test compound dissolved in DMSO. As shown in FIG. 2, three bands of a proform MMP-2, an active intermediate of MMP-2, and an active form of MMP-2 were observed. When the present compound (2-pyrrolylthiochromone) was added, the bands disappeared according to the concentration thereof. It is apparent from the results that the present compound can inhibit the production of MMP-2 according to the concentration thereof.

Example 40: Antitumor activity of 2-pyrrolylthiochromone to mouse melanoma

Mouse melanoma (B16-BL6) cells were subcutaneously implanted in the amount 1×10⁶ cells in C57BL/6N mice (6 weeks old, male) at the axillary fossa. From the day after the implantation, 2-pyrrolylthiochromone was orally administered once a day for 13 days. The composition to be administered was preparedby dissolving 2-pyrrolylthiochromone powder in sesame oil, and administered at the dose of 100 mg of the compound per 1 kg of the mouse body weight. The amount of sesame oil administered was 10 ml/kg of the mouse body weight. To the control group, only sesame oil was administered. At the next day of the last administration day, the mice were sacrificed, and the weight of the tumor was measured. For the control group where the present compound was not administered, five mice were used, whereas 6 mice were used for the group where the present compound was administered.

Figure 3:
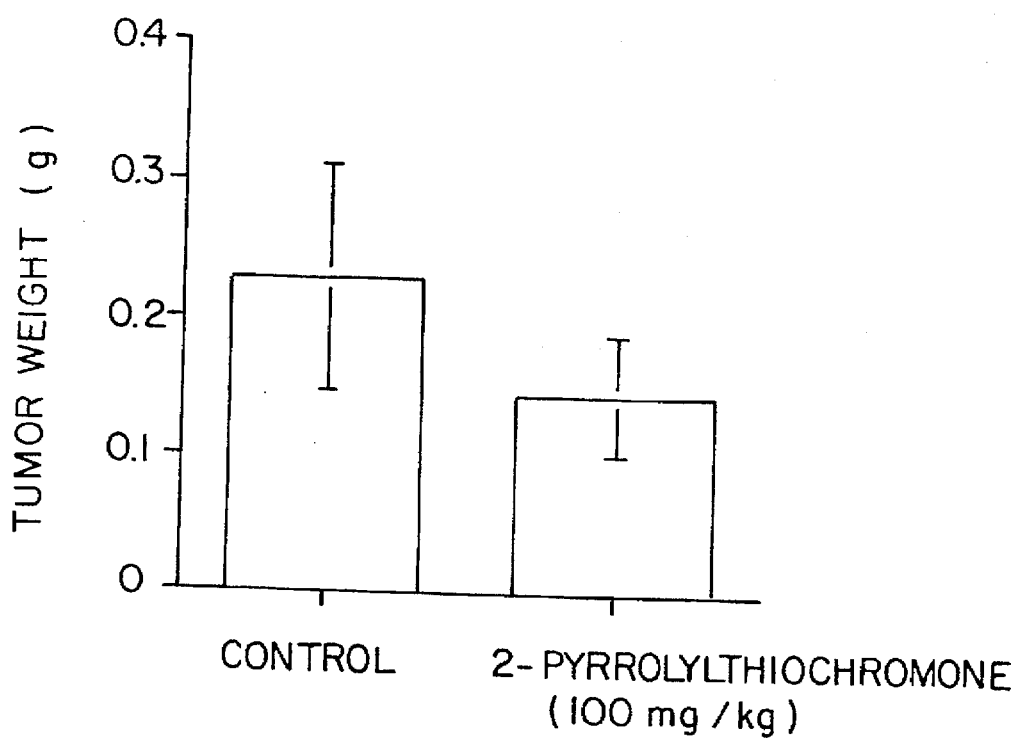
FIG. 3 illustrates an antitumor activity to mouse melanoma-cells-implanted-mouse; see Example 40.

The results are shown in FIG. 3. The group where 100 mg/kg of 2-pyrrolylthiochromone was administered exhibited 36.7% inhibitory activity for the tumor growth in comparison with the control group. Decrease in the body weight due to the administration of 2-pyrrolylthiochromone was not observed.

As explained above, the novel chromone derivative of the present invention inhibits the matrix metalloproteinase, is stable as a medicine, and has low toxicity. Therefore, the chromone derivative of the present invention would be very useful as a pharmaceutical composition as a matrix metalloproteinase inhibitor for the various treatment of infiltration or metastasis of cancer tissue, glomerular nephritis, osteoporosis, or arthropathy, such as rheumatoid arthritis, osteoarthritis, periarthritis humeroscapularis, shoulder-arm-neck syndrome, or lumbago.

Although the present invention has been described with reference to specific embodiments, various changes and modifications obvious to those skilled in the art are deemed to be within the spirit, scope, and concept of the invention.

We claim:

1. A chromone compound of formula (I), or a salt thereof:

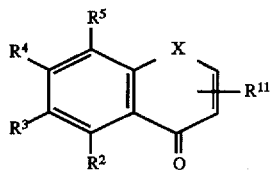

wherein $R^{11}$ is a pyrazolyl, pyrrolyl, triazolyl, benzotriazoly, benzimidazolyl, indazolyl, or indolyl group, $R^2$, $R^3$, $R^4$, and $R^5$ are each independently a hydrogen or halogen atom, or a hydroxy or alkoxy group, or an alkoxy group substituted with one or more alkoxy groups, and X is an oxygen or sulfur atom.

2. The chromone compound according to claim 1, wherein X is a sulfur atom.

3. A pharmaceutical composition comprising a chromone compound of formula (I), or a pharmaceutically acceptable salt thereof:

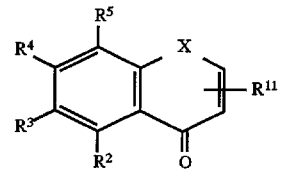

wherein $R^{11}$ is a pyrazolyl, pyrrolyl, triazolyl, benzotriazoly, benzimidazolyl, indazolyl, or indolyl group, $R^2$, $R^3$, $R^4$, and $R^5$ are each independently a hydrogen or halogen atom, or a hydroxy or alkoxy group, or an alkoxy group substituted with one or more alkoxy groups, and X is an oxygen or sulfur atom, and a pharmaceutically acceptable carrier.

4. A method for inhibiting matrix metalloproteinase comprising contacting matrix metalloproteinase with an effective amount of a chromone compound of formula (I), or a pharmaceutically acceptable salt thereof:

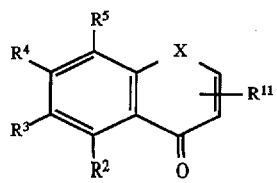

wherein $R^{11}$ is a pyrazolyl, pyrrolyl, triazolyl, benzotriazoly, benzimidazolyl, indazolyl, or indolyl group, $R^2$, $R^3$, $R^4$, $R^5$ are each independently a hydrogan or halogen atom, or a hydroxy or alkoxy group, or an alkoxy group substituted with one or more alkoxy groups, and X is an oxygen or sulfur atom.

5. A method for treatment of a disease associated with matrix metalloproteinase activity, comprising administering to a mammal afflicted with said disease an effective amount of a chromone compound of formula (I), or a pharmaceutically acceptable salt thereof:

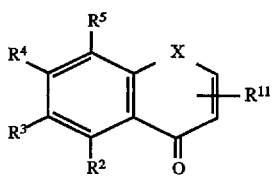

wherein $R^{11}$ is a pyrazolyl, pyrrolyl, triazolyl, benzotriazoly, benzimidazolyl, indazolyl, or indolyl group, $R^2$, $R^3$, $R^4$, and $R^5$ are each independently a hydrogen or halogen atom, or a hydroxy or alkoxy group, or an alkoxy group substituted with one or more alkoxy groups, and X is an oxygen or sulfur atom.

6. The method according to claim 5, wherein said disease is cancer.

* * * * *

UNITED STATES PATENT AND TRADEMARK OFFICE
CERTIFICATE OF CORRECTION

PATENT NO. : 5,698,575
DATED : December 16, 1997
INVENTOR(S) : Koju Watanabe, et. al.

It is certified that error appears in the above-identified patent and that said Letters Patent is hereby corrected as shown below:

In Column 19, line 61 (Claim 1, line 3), change "benzotriazoly" to -- benzotriazolyl --.

In Column 20, line 17 (Claim 3, line 5), change "benzotriazoly" to -- benzotriazolyl --.

In Column 20, line 35 (Claim 4, line 6), change "benzotriazoly" to -- benzotriazolyl --.

In Column 20, line 54 (Claim 5, line 7), change "benzotriazoly" to -- benzotriazolyl --.

Signed and Sealed this

Second Day of June, 1998

Attest:

BRUCE LEHMAN

Attesting Officer

Commissioner of Patents and Trademarks